(12) United States Patent
Zaidel et al.

(10) Patent No.: US 8,792,972 B2
(45) Date of Patent: Jul. 29, 2014

(54) REAL-TIME METHODS AND SYSTEMS FOR MAPPING A TARGET REGION IN THE BRAIN DURING SURGERY

(75) Inventors: Adam Zaidel, Jerusalem (IL); Hagai Bergman, Jerusalem (IL); Zvi Israel, Jerusalem (IL)

(73) Assignee: Alpha Omega Engineering Ltd., Nazareth Illit (IL)

( * ) Notice: Subject to any disclaimer, the term of this patent is extended or adjusted under 35 U.S.C. 154(b) by 383 days.

(21) Appl. No.: 12/658,351

(22) Filed: Feb. 5, 2010

(65) Prior Publication Data
US 2010/0241020 A1    Sep. 23, 2010

Related U.S. Application Data

(60) Provisional application No. 61/202,205, filed on Feb. 5, 2009.

(51) Int. Cl.
*A61B 5/04*    (2006.01)

(52) U.S. Cl.
USPC .............................................. 600/544; 607/2

(58) Field of Classification Search
USPC .................................. 600/544, 545
See application file for complete search history.

(56) References Cited

U.S. PATENT DOCUMENTS

| | | | |
|---|---|---|---|
| 2007/0167856 A1* | 7/2007 | McNames et al. | 600/544 |
| 2008/0195175 A1* | 8/2008 | Balzer et al. | 607/45 |
| 2008/0292052 A1* | 11/2008 | Dilmanian et al. | 378/65 |
| 2010/0204748 A1* | 8/2010 | Lozano et al. | 607/45 |

OTHER PUBLICATIONS

Zaidel et al; "Delimiting Subterritories of the Human Subthalamic Nucleus by Means of Microelectrode Recordings and a Hidden Markov Model" Movement Disorders vol. 24, No. 12, pp. 1785-1793. (2009).
Chen et al; "Intra-operative recordings of local field potentials can help localize the subthalamic nucleus in Parkinson's disease surgery" Experimental Neurology 198, pp. 214-221. (2006).
Herzog et al; "Most Effective Stimulation Site in Subthalamic Deep Brain Stimulation for Parkinson's Disease" Movement Disorders vol. 19, No. 9, pp. 1050-1099. (2004).
Machado et al; "Deep Brain Stimulation for Parkinson's Disease: Surgical Technique and Perioperative Management" Movement Disorders vol. 21, Suppl. 14, pp. S247-S258. (2006).

(Continued)

*Primary Examiner* — Navin Natnithithadha
*Assistant Examiner* — Etsub Berhanu
(74) *Attorney, Agent, or Firm* — Fleit Gibbons Gutman Bongini & Bianco PL; Martin Fleit; Paul D. Bianco (57) ABSTRACT

A real-time method and system to accurately demarcate sub-territories of the subthalamic nucleus area in the brain during surgery, based on microelectrode recordings and a Hidden Markov Model. Root mean square and power spectral density of the microelectrode recordings are used to train and test Hidden Markov Model in identifying the dorsolateral oscillatory region and non-oscillatory sub-territories within the subthalamic nucleus. After the dorsolateral oscillatory region in the subthalamic nucleus is mapped, the microelectrodes are removed, and a macroelectrode is inserted in the mapped dorsolateral oscillatory region for producing deep brain simulation for treatment of Parkinson's disease.

9 Claims, 4 Drawing Sheets
(2 of 4 Drawing Sheet(s) Filed in Color)

(56) References Cited

OTHER PUBLICATIONS

Moran et al; "Real-Time Refinement of Subthalamic Nucleus Targeting Using Bayesian Decision-Making on the Root Mean Square Measure" Movement Disorders vol. 21, No. 9, pp. 1425-1431. (2006).

Novak et al; "Detection of the subthalamic nucleus in microelectrographic recordings in Parkinson disease using the high-frequency (.500 Hz) neuronal background" J Neurosurg 106, pp. 175-179. (2007).

Danish et al; "Determination of Subthalamic Nucleus Location by Quantitative Analysis of Despiked Background Neural Activity From Microelectrode Recordings Obtained During Deep Brain Stimulation Surgery" Journal of Clinical Neurophysiology vol. 25, No. 2, pp. 98-103. (2008).

Falkenberg et al; "Automatic Analysis and Visualization of Microelectrode Recording Trajectories to the Subthalamic Nucleus: Preliminary Results" Stereotact Funct Neurosurg vol. 84, pp. 35-44 (2006).

* cited by examiner

REAL-TIME METHODS AND SYSTEMS FOR MAPPING A TARGET REGION IN THE BRAIN DURING SURGERY

The patent or application file contains at least one drawing executed in color. Copies of this patent or patent application publication with color drawing(s) will be provided by the Office upon request and payment of the necessary fee.

CROSS-REFERENCE TO RELATED APPLICATIONS

This application claims the benefit of U.S. Provisional Patent Application No. 61/202,205, filed Feb. 5, 2009, of which is incorporated by reference herein.

TECHNICAL FIELD

The present invention relates to mapping regions in the brain using electrophysiology in general, and in particular to a real-time method and system for mapping a the dorsolateral oscillatory region of the subthalamic nucleus in the brain during surgery using a dynamic Bayesian network.

BACKGROUND ART

Deep brain stimulation (DBS) is a surgical procedure involving the implantation of a medical device called a macroelectrode (also referred to as a "lead", "brain pacemaker", "electrode" or "chronic electrode"), which sends electrical impulses to specific parts of the brain. DBS in select brain regions has provided noticeable therapeutic benefits for otherwise treatment-resistant movement and affective disorders such as chronic pain, Parkinson's disease, tremor, dystonia and depression. At present, the procedure is used only for patients whose symptoms cannot be adequately controlled with medications. DBS directly changes brain activity in a controlled manner, and its effects are reversible (unlike those of lesioning techniques).

DBS uses the surgically implanted, battery-operated medical neurostimulator to deliver electrical stimulation to targeted areas in the brain that control movement, blocking the abnormal nerve signals that cause tremor and PD symptoms.

Before the procedure, a neurosurgeon uses magnetic resonance imaging (MRI) or computed tomography (CT) scanning to identify and locate the exact target within the brain. For treating movement disorders, these targets are areas that control movement, such as the thalamus, subthalamic nucleus, and globus pallidus where electrical nerve signals generate the undesired symptoms.

The DBS system consists of three components: the macroelectrode, the extension, and the neurostimulator. The macroelectrode—a thin, insulated wire—is inserted through a small opening in the skull and implanted in the brain. The tip of the electrode is positioned within the targeted brain area.

The extension is an insulated wire that is passed under the skin of the head, neck, and shoulder, connecting the lead to the neurostimulator. The neurostimulator (the "battery pack") is the third component and is usually implanted under the skin near the collarbone. In some cases it may be implanted lower in the chest or under the skin over the abdomen.

Once the system is in place, electrical impulses are sent from the neurostimulator up along the extension wire and the lead and into the brain. These impulses interfere with and block the electrical signals that cause the undesired symptoms. The person has the possibility turn the DBS off if required.

Accurate placement of the macroelectrode is critical in order to improve the effectiveness of the installed macroelectrode. There is thus a need in the field to map in the most precise manner available, the target region for inserting a macroelectrode.

SUMMARY OF INVENTION

It is an object of the present invention to propose a real-time method for mapping a region in the brain during surgery.

It is another object of the present invention to propose a real-time method for mapping a region in the brain during surgery by using a dynamic Bayesian network.

It is a further object of the present invention to propose a real-time method for mapping a region in the brain during surgery by using a Hidden Markov Model (HMM).

It is yet another object of the present invention to propose a real-time method for mapping the dorsolateral oscillatory region (DLOR) of the subthalamic nucleus (STN) in the brain during surgery.

In one aspect, the present invention thus relates to a method for real-time mapping during surgery of the dorsolateral oscillatory region (DLOR) of the subthalamic nucleus (STN), the method comprising the steps of:

(i) inserting one or more electrodes to the brain according to a predetermined insertion trajectory;

(ii) advancing the one or more electrodes towards the estimated location of the DLOR of the STN;

(iii) recording neurophysiological activity by the one or more electrodes along the insertion trajectory;

(iv) calculating power spectral analysis values for the neurophysiological activity recorded along the insertion trajectory; and (v) using a Dynamic Bayesian Network based on part or all of the calculated power spectral analysis values along the insertion trajectory to assign to each selected point along the insertion trajectory one of the following regions with the highest probability value: 1. the DLOR of the STN; 2. the region in the insertion trajectory before the STN; 3. the region inside the nonoscillatory STN; or 4. the region in the insertion trajectory after the STN.

In certain embodiments, the method further comprises the step of removing the one or more electrodes and inserting a macroelectrode in the identified DLOR of the STN for producing deep brain simulation for treatment of Parkinson's disease.

In certain embodiments, the one or more electrodes are microelectrodes, macroelectrodes or both. Microelectrodes offer a higher resolution of the data by being able to advance in smaller-size steps, but it is also possible to use macroelectrodes. It is also possible to combine insertion of both microelectrodes and macroelectrodes.

In certain embodiments, the one or more electrodes are advanced towards the estimated location of the DLOR of the STN continuously; in small discrete steps of equal size; in small discrete steps of variable size; or any combination thereof. For example, it is possible to advance continuously with the electrode(s) until arriving to a destination point. Alternatively, it is possible to advance continuously with the electrode(s), until a certain point and then advance in discreet steps of a fixed or variable size.

In certain embodiments, the power spectral analysis values are obtained by using power spectral density (PSD) calculations though it is possible to use other power spectral analysis methods according to the invention.

In certain embodiments, the method further comprises the step of calculating normalized Root mean square (NRMS) values for the recorded neurophysiological activity.

In certain embodiments, the Dynamic Bayesian Network is a Hidden Markov Model (HMM) though it is possible to use other Dynamic Bayesian Network algorithms with the invention.

In certain embodiments, the method further comprises an initial step of training the Dynamic Bayesian Network by providing reference data of a statistically-significant number of insertion trajectories wherein points along each insertion trajectory are assigned by an expert to one of the following regions: 1. the DLOR of the STN; 2. the region in the insertion trajectory before the STN; 3. the region inside the nonoscillatory STN; or 4. the region in the insertion trajectory after the STN.

The present invention also relates to a system for real-time mapping during surgery of the dorsolateral oscillatory region (DLOR) of the subthalamic nucleus (STN), the system comprising:

(i) one or more electrodes inserted into the brain according to a predetermined insertion trajectory;

(ii) advancing means for advancing the one or more electrodes towards the estimated location of the DLOR of the STN;

(iii) a recording unit for recording neurophysiological activity by the one or more electrodes along the insertion trajectory;

(iv) first data processing means for calculating power spectral analysis values for the neurophysiological activity recorded along the insertion trajectory; and (v) second data processing means for using a Dynamic Bayesian Network based on part or all of the calculated power spectral analysis values along the insertion trajectory to assign to each selected point along the insertion trajectory one of the following regions with the highest probability value: 1. the DLOR of the STN; 2. the region in the insertion trajectory before the STN; 3. the region inside the nonoscillatory STN; or 4. the region in the insertion trajectory after the STN.

The first and second data processing means can be implemented in a computer system.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIGS. 3A-3D are graphs showing an HMM transition inference example. FIG. 3A—PSD, same conventions as in FIG. 1B. FIG. 3B—NRMS, same conventions as in FIG. 1A. FIG. 3C—Cyan and magenta lines represent the mean and maximum beta PSD, respectively. Beta PSD per EDT=10× $\log_{10}$, (PSD power/average PSD power). FIG. 3D The blue and green lines represent the cluster observation sequence (tags) and the HMM state inference (states, as defined in FIG. 2), respectively.

DESCRIPTION OF EMBODIMENTS

In the following detailed description of various embodiments, reference is made to the accompanying drawings that form a part thereof, and in which are shown by way of illustration specific embodiments in which the invention may be practiced. It is understood that other embodiments may be utilized and structural changes may be made without departing from the scope of the present invention.

Treating Parkinson Disease

1. General Discussion

Surgical treatment for advanced Parkinson's disease (PD) includes deep brain stimulation (DBS) of the subthalamic nucleus (STN), which has proven to be safe and beneficial over time. During surgery for implanting an STN DBS macroelectrode, microelectrode recording (MER) is often utilized to verify localization of the STN physiologically. To implant the macroelectrode successfully within the optimal location (probably the sensorimotor portion of the STN), accurate demarcation of the patient's STN (based on the MERs) is required. This includes derivation of the entry and exit points of the STN across the MER trajectory, as well as localization of the sensorimotor area within the STN.

It has been well established that the STN can be divided into three (sensorimotor, limbic, and cognitive/associative) functional territories, each broadly involved in its respective basal ganglia-thalamocortical loop. The sensorimotor region of the STN is primarily located dorsolaterally, the same location that seems to provide optimal therapeutic benefit to patients undergoing STN DBS.

Furthermore, it has been shown that local field potential and single unit (when averaged across patients) beta oscillatory activity is generated largely within the dorsolateral portion of the STN. It would therefore seem that there is correspondence between the dorsolateral oscillatory region (DLOR) and the sensorimotor region of the STN, and that beta-oscillatory activity could possibly predict the most effective contact for STN DBS.

Such a method could aid the neurosurgeon in implanting the macroelectrode in the optimal location or simply be used to estimate the transitions of a MER trajectory. Automatic methods have been described to identify the entry and exit points of the STN; however, to the best of our knowledge there is no physiological method described to date that identifies subterritories within the STN. We present a real-time method to delimit the outer boundaries of the STN as well as an intra-STN (DLOR-ventral) boundary during surgery based on the root mean square (RMS) and power spectral density (PSD) of the MERs, using a Hidden Markov Model (HMM).

2. Patients and Methods

Patients and MERs activity was recorded via polyimide coated tungsten microelectrodes (AlphaOmega) with impedance mean±standard deviation (SD): 0.64±0.14 MΩ (measured at 1 kHz at the

TABLE 1

Patient details

| | Age (yrs) | Gender | Disease duration (yrs) | UPDRS Before DBS | | Months since DBS | UPDRS After DBS | | | | Medications (LEDD*) daily doses | | |
|---|---|---|---|---|---|---|---|---|---|---|---|---|---|
| | | | | | | | On Stim | | Off Stim | | Before STN DBS | Months since DBS | After STN DBS |
| | | | | On Med | Off Med | | On Med | Off Med | On Med | Off Med | | | |
| Patient-1 | 73 | F | 14 | 31 | 70 | NA | NA | NA | NA | NA | 2250 | 3 | 950 |
| Patient-2 | 51 | F | 14 | 17 | 99 | 13 | 2 | 16 | 9 | 46 | 1700 | NA | 875 |
| Patient-3 | 68 | M | 9 | NA | NA | NA | NA | NA | NA | NA | 1662.5 | NA | 1246.9 |
| Patient-4 | 69 | M | 10 | 32 | 65.5 | NA | NA | NA | NA | NA | 375 | NA | 412.5 |
| Patient-5 | 61 | F | 11 | NA | NA | 10 | 11 | NA | NA | 54 | 1087 | 9 | 0 |
| Patient-6 | 58 | M | 22 | 22.5 | 55 | 8 | 5 | 14 | 61 | 64 | 2575 | 8 | 900 |
| Patient-7 | 57 | M | 10 | NA | NA | 8 | 0 | 14 | NA | 65 | 1250 | 8 | 250 |
| Patient-8 | 73 | M | 6 | 22 | 55 | 4 | 5 | 18 | NA | NA | 1700 | NA | 700 |
| Patient-9 | 50 | M | 8 | 29 | 79 | 2 | 14 | 12 | 47 | 54 | 379.5 | NA | 259.5 |
| Patient-10 | 75 | F | 8 | 17 | 51 | 8 | 17 | 21 | 24 | 37 | 1400.1 | 7 | 897.8 |
| Patient-11 | 61 | M | 6 | 20 | 47 | 8 | 10 | 25 | NA | NA | 399 | 6 | 266 |
| Patient-12 | 61 | F | 5 | 38 | 73 | 8 | 1 | 10 | NA | 47 | 1250 | 5 | 125 |
| Patient-13 | 56 | M | 8 | 29 | 70 | NA | NA | NA | NA | NA | 875 | NA | 250 |
| Patient-14 | 63 | F | 12 | 19 | 49 | 3 | 5 | 16 | NA | NA | 890 | NA | 459 |
| Patient-15 | 49 | M | 10 | 4 | 44 | NA | NA | NA | NA | NA | 900 | NA | NA |
| Patient-16 | 64 | F | 11 | 3 | 21 | 5 | 2 | 4 | 7 | 21 | 1505 | 4 | 437.5 |
| Patient-17 | 52 | M | 9 | 13 | 49.5 | 1 | 6 | 22 | NA | 34 | 1300 | 3 | 312.5 |
| Patient-18 | 59 | M | 8 | 13 | 72 | 1 | 9 | 30 | NA | 49 | 725 | NA | 248.7 |
| Patient-19 | 61 | M | 6 | 32 | 60 | 3 | 10 | 14 | 51 | 61 | 700 | 2 | 200 |
| Patient-20 | 55 | M | 7 | 21 | 37 | 3 | 8 | 15 | 17 | 21 | 740 | NA | 426 |
| Patient-21 | 66 | F | 15 | NA | NA | NA | NA | NA | NA | NA | 1540 | 3 | 375 |
| Mean | 61.0 | 38% F | 10.0 | 21.3 | 58.6 | 5.7 | 7.0 | 16.5 | 30.9 | 46.1 | 1200.1 | 5.3 | 479.6 |

*LEDD, Levodopa equivalent daily dose as calculated by Deuschl et al.;
DBS, Deep brain stimulation;
Med, medication;
Stim, Stimulation;
UPDRS, Unified Parkinson's Disease Rating Scale - motor section (section 3, maximum = 108);
NA, not available.

The MERs from 21 PD patients undergoing bilateral STN DBS implantation were analyzed (patient details are presented in Table 1). All patients met accepted selection criteria for STN DBS and signed informed consent for surgery with MER.

This study was authorized and approved by the Institutional Review Board of Hadassah University Hospital in accordance with the Declaration of Helsinki. No sedative was used and all patients were awake during surgery. The patient's level of awareness was continuously assessed clinically, and when drowsy the patient was stimulated and awoken through conversation by a member of the surgical team. Data were obtained off dopaminergic medications (>12 hours since last medication) and during periods of rest. Further details of the surgical procedure and data acquisition are presented as supplementary material.

Surgical Procedure and Data Acquisition Details

Surgery was performed using the CRW stereotactic frame (Radionics, Burlington, Mass., USA). STN target coordinates were chosen as a composite of indirect anterior commissure-posterior commissure atlas based location and direct T2 magnetic resonance imaging (MRI), using Framelink 4 or Framelink 5 software (Medtronic, Minneapolis, USA). The position of the implanted STN DBS electrodes was verified on postoperative computerized tomography (CT) fused with the preoperative MRI (also using Framelink software).

Data were acquired with the MicroGuide system (Alpha-Omega Engineering, Nazareth, Israel). Neurophysiological beginning of each trajectory). The signal was amplified by 10,000, band-passed from 250 to 6,000 Hz (using a hardware four-pole Butterworth filter) and sampled at 48 kHz by a 12 bit A/D converter (using ±5 V input range, i.e. ~0.25 μV amplitude resolution). One trajectory was mistakenly sampled at 12 kHz/

For both the left and right hemispheres, a single trajectory using one or two microelectrodes (separated by 2 mm anteroposteriorly in the parasagittal plane) was made starting at 10 mm above the calculated target (center of the lateral STN). The electrodes were advanced in small discrete steps, toward the estimated center of the lateral STN. Step size (ranging 500 μm down to 50 μm in our recordings) was controlled by the neurophysiologist in order to achieve optimal unit recording and identification of upper and lower borders of the STN. Typically, shorter steps (~100 lm) were used when the electrode was advanced closer to the presumed location of the STN. Following a 2-second signal stabilization period after electrode movement cessation, multi-unit traces were recorded for a minimum of 5 seconds.

Stability Inclusion Criteria

Conditions in the operating-room often result in non-stable recordings (e.g. due to further movement of brain tissue in relation to the electrode tip or due to neuronal injury). The data traces were therefore analyzed for stability by custom software. This was done by dividing each data trace into consecutive segments of 50 ms and computing the root mean square (RMS, see below) for each segment. A section of the trace was considered stale when all corresponding segments' RMS values lay within three standard deviations of the media RMS. The longest stable section of the data trace was then selected for further analysis, discarding the rest of the trace. All stable sections included in the analysis were longer than 3 seconds (duration mean±SD: 10.8±3.4 s). This type of stability analysis rejects infrequent events such as glitches or cell injury but does not reject oscillatory activity. Only electrodes that passed through the STN were used for this study (56 in total).

The Root Mean Square (RMS)

Entry and exit from the STN are marked primarily by a dramatic increase and decrease in normalized RMS (NRMS), respectively. In addition, PSD can be used as a marker for the DLOR of the STN based on the increased beta oscillatory activity. The NRMS and PSD of an example trajectory, as a function of estimated distance to target (EDT), are presented in FIGS. 1A and 1B accordingly.

The RMS estimate of the raw multi-unit activity recorded by the microelectrode at each electrode depth (step) is defined as follows (Eq. 1):

$$\text{RMS}(\overline{X}) = \sqrt{\frac{\sum_{i=1}^{n}(X_i - \mu)^2}{n-1}} \quad (1)$$

where $\overline{X}$ is the vector of a sampled analog signal with mean $\mu$, $X_i$ is each sample, and n is the number of samples. RMS values are susceptible to electrode properties and other external factors (e.g. amplifier gain); hence the RMS requires normalization in order to be an absolute measure. The RMS for each trajectory was therefore normalized by the RMS average of the first ten recordings (assumed to represent an unbiased estimate of the pre-STN baseline activity) creating a normalized RMS (NRMS; see FIG. 1A).

The Power Spectral Density (PSD)

For the power spectral density (PSD) calculations, the raw signal was rectified by the "absolute" operator and the mean subtracted. This procedure was required in order to expose the frequency band of interest (below 70 Hz) since the original analog data was band-pass filtered at 250-6,000 Hz (due to constraints of the operating room). The average PSD was calculated in each trace using Welch's method with a 1 second Hamming window (with 50% overlap) and zero padding, resulting in a spectral resolution of ⅓ Hz. For each recording, the PSD was normalized by the total power of the signal between 2-200 Hz (excluding the PSD within 2.5 Hz of the 50 Hz power supply artifacts and their harmonics). A plot of the PSD as a function of estimated distance to target (EDT) for an example trajectory (Patient 17, right STN in Table 1; the same one for which the RMS is demonstrated in FIG. 1A) can be seen in FIG. 1B. When plotting the PSD, the 50 Hz power supply artifacts and their harmonics were replaced by the mean PSD, and the PSD was smoothed in the frequency direction using a narrow Gaussian window (SD=0.33 Hz).

The Hidden Markov Model

A HMM was used to estimate the state of the electrode at each step (depth) across the trajectory based on the NRMS and PSD of the MERs. Four discrete states were defined:
1. Before the STN
2. In the DLOR of the STN
3. In the nonoscillatory STN
4. Out of the STN A typical trajectory state sequence would go through all four states consecutively. However, not all trajectories had oscillatory recordings in the presumed dorsolateral region of the STN; hence, a trajectory could skip state 2. In addition, it was possible for a trajectory to end in state 3 (a MER trajectory that was terminated before exiting the STN). In the advancement of a sequence, it was possible to remain in the same state, but not possible to go backwards (e.g., from a state within the STN to "before the STN" state). Trajectories that did not pass through the STN were not included in this study because they are a trivial case for which the RMS remains at baseline level throughout the trajectory and there are no transitions. (For an online application, it could be easily tested whether the RMS has a minimum increase before applying the HMM to the trajectory.)

An HMM state sequence uniquely defined three possible state transitions:
  i. In: STN entry (noted by transition from state 1 to state 2 or state 3).
  ii. DLOR-ventral: the ventral boundary of the DLOR (noted by transition from state 2 to state 3).
  iii. Out: STN exit (noted by transition from state 3 to state 4).

Figure 2:
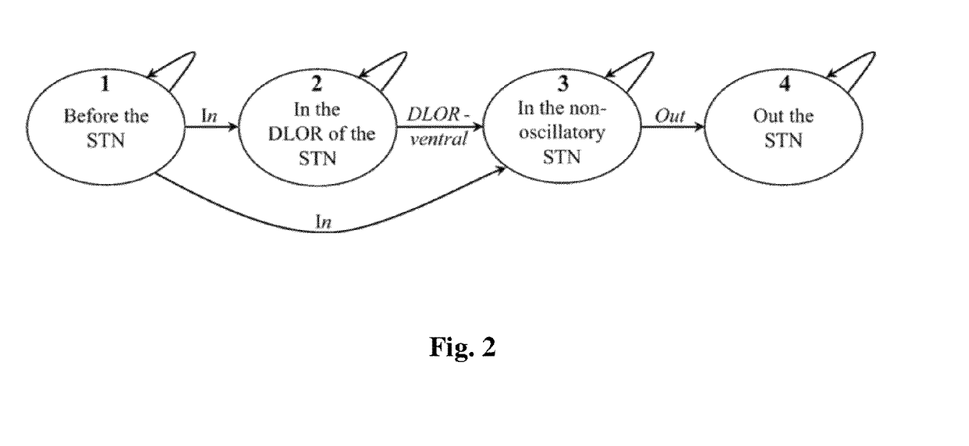
FIG. 2 shows the four possible HMM states. Arrows represent the three possible states transitions (In, DLOR-ventral, and Out) and the possibility of staying in the same state with no transition (reflexive arrows).

A scheme of the possible HMM states and transitions can be seen in FIG. 2.

Data Observations and Clustering

In order to best estimate the hidden state, the following observations were used:
  1. The normalized root mean square (NRMS)
  2. The mean beta (13-30 Hz) PSD
  3. The maximum beta PSD Since the data set was limited (56 trajectories), it was necessary to have a relatively small HMM "emission" matrix (the matrix depicting the probability of each observation per HMM state) otherwise it wouldn't be adequately sampled during the learning stage. This requirement limited the resolution with which the three different observation quantities could be quantized since the number of possible combinations defines the order of the matrix. A custom method of coarse (yet logical, as will be explained below) quantization was adopted, whereby the observations were grouped into six clusters as follows:

All observations with NRMS<1.25 (threshold 1), i.e. below a 25% increase from the NRMS baseline (which is equal to 1 due to the normalization) were clustered together (Low-NRMS cluster).

The mean deviation from threshold 1 (i.e. NRMS ≥ 1.25) of the remaining observations was calculated. Threshold 2 was defined by threshold 1 plus 25% of the calculated mean deviation. Observations with NRMS between threshold 1 and threshold 2 were clustered together (Intermediate-NRMS cluster), while observations with NRMS>threshold 2 where further divided according to their (maximum and mean) beta oscillatory activity (above or below the median), resulting in a further four (high-NRMS) clusters (a detailed breakdown of these clusters can be seen in Table 2).

Figure 3A:
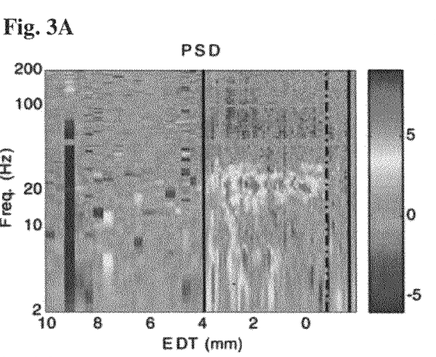
Figure 3B:
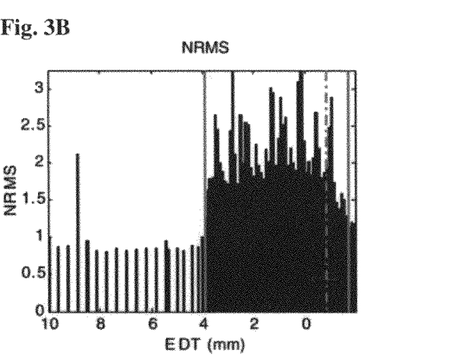
Figure 3C:
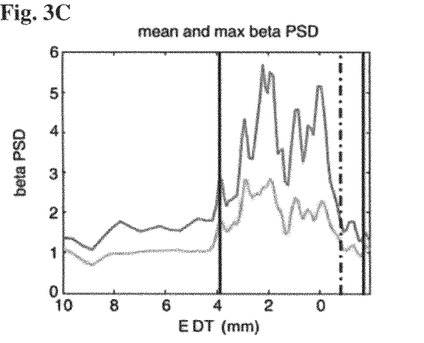

The reasoning behind the clustering method can be explained as follows: In clustering the NRMS, using an "absolute" threshold (threshold 1) was appropriate since the RMS was normalized. However, as we have previously reported, there exists interpatient variability of NRMS within the STN; hence, it is also appropriate to have a "relative" threshold in addition (threshold 2) particular to each trajectory. The NRMS values (and less so PSD) are important in deciding In/Out transitions; hence, PSD was not taken into account for low NRMS values. However, for high NRMS (>threshold 2), the observations were further clustered based on the PSD since the DLOR-ventral transition (based on PSD) takes place at high values of NRMS (i.e. within the STN). It was noted that some patients had a narrow band of beta oscillatory activity (e.g. FIG. 1B), whereas others had a wider band (e.g. FIG. 3A). We assumed that maximum and mean beta PSD would better capture the narrow and wide band beta oscillations, respectively. Both mean and maximum (beta oscillatory activity) were used for PSD clustering. Tremor frequency oscillations seemed to be episodic and sporadic. They were not always present and when present they did not define a continuous region as the beta oscillations did (FIG. 3A). We therefore did not incorporate them into the HMM.

Estimating and Testing the HMM

Figure 1A:
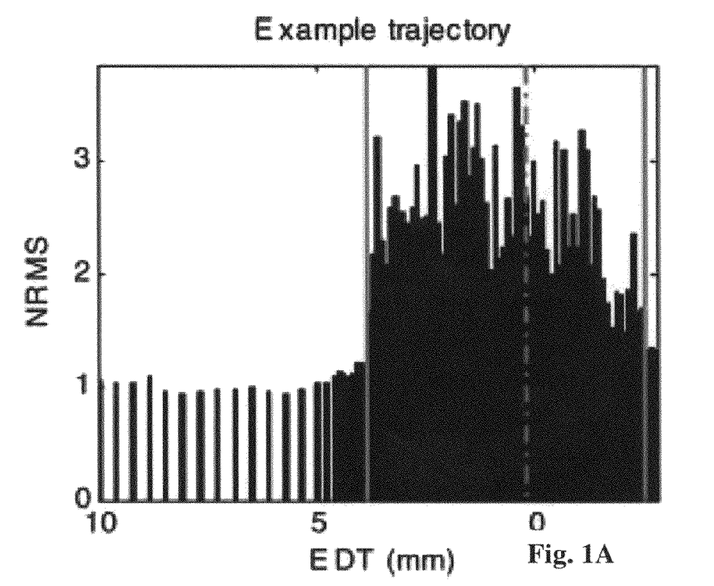
FIG. 1A is a graph showing the normalized root mean square (NRMS) of an example trajectory as a function of estimated distance to target (EDT).
Figure 1B:
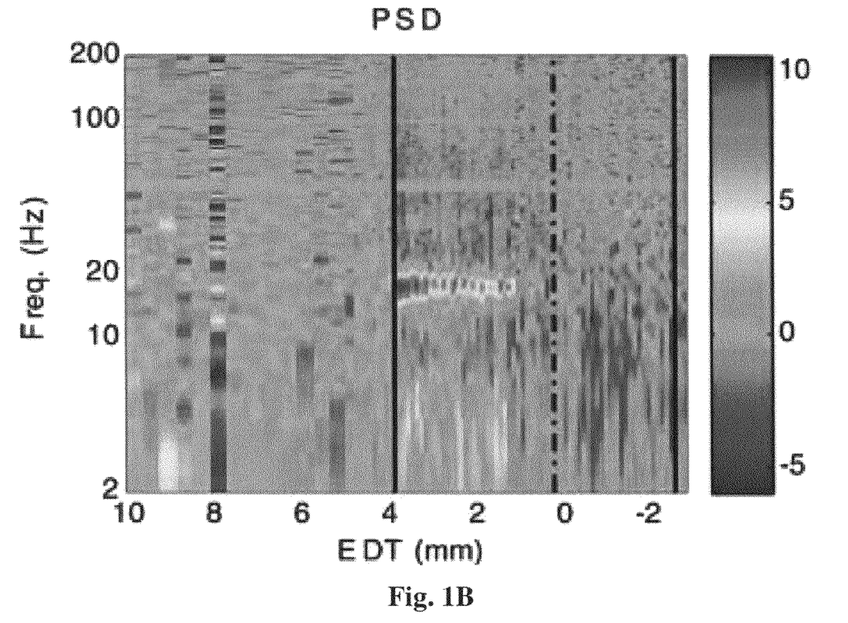
FIG. 1B is a graph showing the PSD of the same trajectory. The PSD color-scale represents 10×log 10 (PSD power/average PSD power) per EDT. The red (A) and black (B) solid vertical lines indicate STN entry and exit; the dot-dash lines indicate the ventral boundary of the dorsolateral oscillatory region (DLOR).

For each trajectory, the "known" state transitions were defined (corresponding to the three possible HMM state transitions—mentioned earlier in section The Hidden Markov model). In (STN entry) and Out (STN exit) transitions were based on intraoperative neuronal analysis by the neurophysiologist as well as the NRMS plots, and the DLOR-ventral transition was distinguished by visual inspection of the PSD by one of the authors (AZ)—noting a sudden decrease in beta oscillatory activity. The known state transitions are depicted in the NRMS plots by red lines and in the PSD plots by black lines (FIGS. 1 and 3). These transitions defined a known state sequence for estimating and testing the HMM.

The maximum likelihood estimate of the HMM transition and emission probability matrices were estimated based on the known (human expert defined) state sequences. Since the training data were fully labeled (there were known state sequences for the whole dataset), there was no need for the expectation-maximization (EM) algorithm or iterative procedures (which would require initial guessing of the probability matrices), and the matrices could be directly estimated. The HMM was estimated using the known state sequences of all trajectories excluding one (N−1=55), and then tested on the excluded trajectory (with no assumption of its sequence) by comparing the inferred HMM state transitions to the trajectory's known state transitions. The inferred HMM state sequence was calculated as the most probable sequence beginning with the HMM in state 1 before the first observation (using the Viterbi algorithm). This method was repeated N (56) times, testing each trajectory individually. The mean and SD of the error in estimating each of the three transitions were calculated.

HMM Parameters and Robustness

It was thought that use of EDT (as in the Bayesian method) would aid the HMM. However, coarse clustering by EDT did not improve the results and therefore was not used.

The NRMS clustering was accomplished by only a limited amount of coarse, manual tuning. We set a percentage parameter (P) for the thresholds to be 25%, i.e. clustering was done by P (25%) increase from the NRMS baseline (threshold-1) and P (25%) of the mean deviation from threshold-1, defined as threshold-2 (see method section Data observations and clustering above). In order to test robustness to threshold variation we varied P from 15% to 40% affecting both thresholds. A comparison of the results is presented as Table 3. The detection reliabilities, error means and SDs both for reduced (P=15%) and increased (P=40%) thresholds were similar to the results presented above (and sometimes even better), indicating robustness to limited threshold variation. In and DLOR-ventral detections were particularly robust, with Out detections being slightly more sensitive to threshold variation.

TABLE 3

Results comparison for threshold variation and removal of stability analysis

| | | Reduced threshold (P = 15%) | Default threshold (P = 25%) | Increased threshold (P = 40%) | Without stability analysis |
|---|---|---|---|---|---|
| In | Reliability | 100% | 100% | 100% | 100% |
| | Error (mm) | −0.10 ± 0.34 | −0.09 ± 0.35 | −0.02 ± 0.35 | −0.08 ± 0.37 |
| DLOR-ventral | Reliability | 96% | 98% | 95% | 96% |
| | Error (mm) | −0.23 ± 0.56 | −0.27 ± 0.58 | −0.30 ± 0.62 | −0.33 ± 0.65 |
| Out | Reliability | 86% | 93% | 86% | 84% |
| | Error (mm) | −0.06 ± 0.39 | −0.20 ± 0.33 | −0.39 ± 0.59 | −0.34 ± 0.52 |

The column marked P=25% presents the nominal results for the default value used in this manuscript. The other columns demonstrate robustness of the results to threshold perturbation and removal of stability analysis (with default threshold). Reliability=percentage of correct detections from the total. Error is given as mean±standard deviation.

Threshold robustness was also apparent in the PSD, since median alone was used as the PSD threshold for clustering. (Varying the threshold from 40th to 60th percentiles instead of median produced similar results—data not shown). Using both mean and maximum beta PSD (clustered above or below the respective median) provided better results than using one alone.

Robustness was also tested by training and testing the HMM on the raw data without automatic stability analysis (presented hereinabove in the section stability inclusion criteria). Here too, results (see Table 4) were similar, with Out detections being the most sensitive. Hence, on the whole, the method is robust to threshold variation and data instability, with Out detection reliability being the most sensitive due to additional Out detection misses.

Software

Data analysis was carried out on custom software, MATLAB V7.1 (Mathworks, Natick, Mass.), using MATLAB HMM toolbox. This software can be found online (http://basalganglia.huji.ac.il/links.htm).

2. Results

Distinct DLOR

The description of beta oscillations in the STN to date has generally been derived from pooling data across patients. The pooled data presents a gradient of beta oscillatory activity (more oscillations dorsally; less ventrally) giving the impression of a continuum, without a distinct dorsal-ventral border. Such a mean gradient however does not necessitate that each patient/trajectory has a gradient. Rather it can arise from the pooling of numerous trajectories, each of which has a distinct oscillatory/nonoscillatory boundary but at different depths. The individual trajectories we analyzed demonstrated the existence of a distinct DLOR boundary and not a gradient (FIGS. 1B and 3A). Some trajectories had a short DLOR and others had a longer DLOR (sometimes extending far ventrally) and when pooled the heterogeneous trajectories average to a gradient of beta oscillatory activity. We therefore propose that each trajectory has a distinct boundary (at a particular depth) that can be visually discerned and automatically detected by an HMM.

HMM State Inference

For each of the 56 trajectories, the HMM was estimated individually based on the other 55 trajectories. The resulting mean HMM transition and emission matrices are presented in Table 2A and Table 2B.

TABLE 2A

The HMM transition and emission matrices

| Transition matrix | | To | | | |
|---|---|---|---|---|---|
| | | State-1 | State-2 | State-3 | State-4 |
| From | State-1 | 0.946 | 0.047 | 0.007 | 0 |
| | State-2 | 0 | 0.956 | 0.044 | 0 |
| | State-3 | 0 | 0 | 0.964 | 0.036 |
| | State-4 | 0 | 0 | 0 | 1.000 |

Table 2A depicts the HMM transition matrix. Values depict the probability of transition between states (or remaining in the current state) for each step of the sequence.

The columns (State-1 to State-4) depict a current location. The rows (State-1 to State-4) depict the next location in the insertion trajectory. The value in the cell is the probability of going from one state to another state, given the current state in the insertion trajectory.

For example, when in State-1 there is a 0.946 probability of remaining in State-1, a 0.047 probability of transitioning to State-2, a 0.007 probability of transitioning to State-3, and a zero probability of transitioning to State-4 (in this case, we cannot go directly from "before the STN" to "after the STN" without first going through the STN).

TABLE 2B

The HMM transition and emission matrices

| Emission matrix | | Observations | | | | | |
|---|---|---|---|---|---|---|---|
| | | | | high-NRMS | | | |
| | | | | High mean beta | | Low mean beta | |
| | | Low-NRMS tag-1 | Intermediate-NRMS tag-2 | High max beta tag-3 | Low max beta tag-4 | High max beta tag-5 | Low max beta tag-6 |
| State | State-1 | 0.955 | 0.025 | 0.006 | 0.008 | 0.005 | 0.008 |
| | State-2 | 0.031 | 0.057 | 0.752 | 0.047 | 0.047 | 0.065 |
| | State-3 | 0.045 | 0.076 | 0.109 | 0.042 | 0.083 | 0.645 |
| | State-4 | 0.633 | 0.247 | 0.003 | 0.006 | 0.007 | 0.105 |

Table 2B depicts the HMM emission matrix. Values depict the probability of each observation given the state. Numerical tags correspond to the six clusters of NRMS and beta observations detailed in the table header. States: 1—before the STN; 2—in the dorsolateral oscillatory region (DLOR) of the STN; 3—in the non-oscillatory STN; 4—out the STN.

Given the NMRS and PSD values obtained, it was advantageous not to work with the raw (discrete) NMRS and PSD values, but to first reduce the probability space to six clusters identified in Table 2B as tag-1 to tag-6. The clustering criteria are shown in Table 2B, for example, low NMRS values were classified as tag-1; intermediate NMRS values were classified as tag-2. Recordings with high NMRS values were further divided into 4 clusters (tag-3 to tag-6) in accordance with the mean beta and high beta values.

Figure 3D:
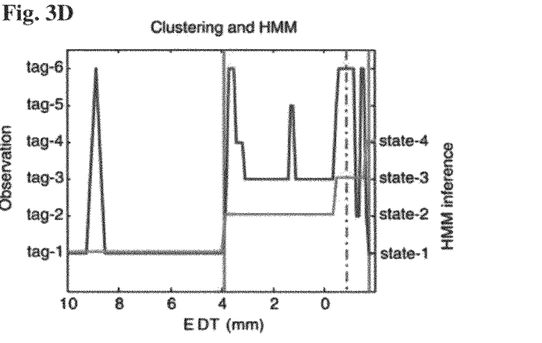
Figure 4A:
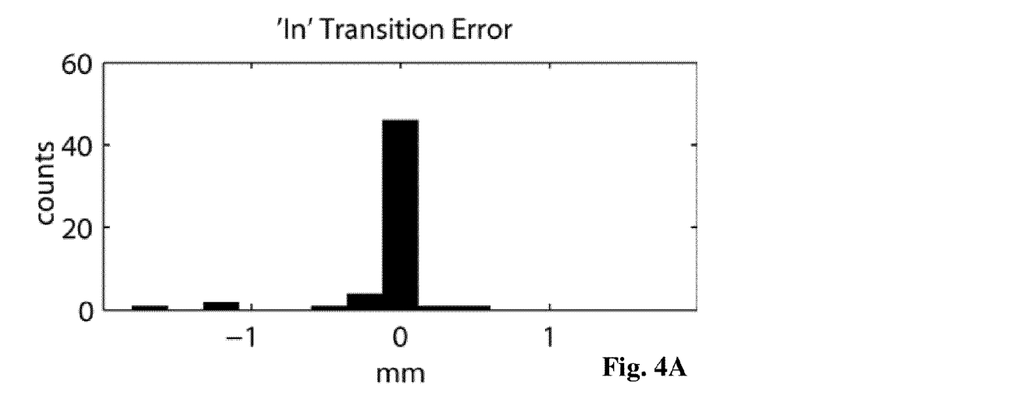
FIGS. 4A-4C are histograms showing the HMM transition error histograms for In (FIG. 4A), DLOR-ventral (FIG. 4B), and Out (FIG. 4C) state transitions.
Figure 4B:
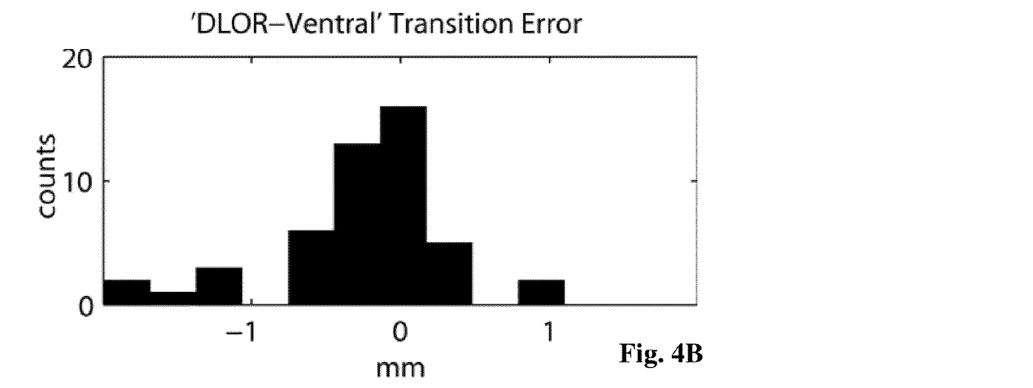
Figure 4C:
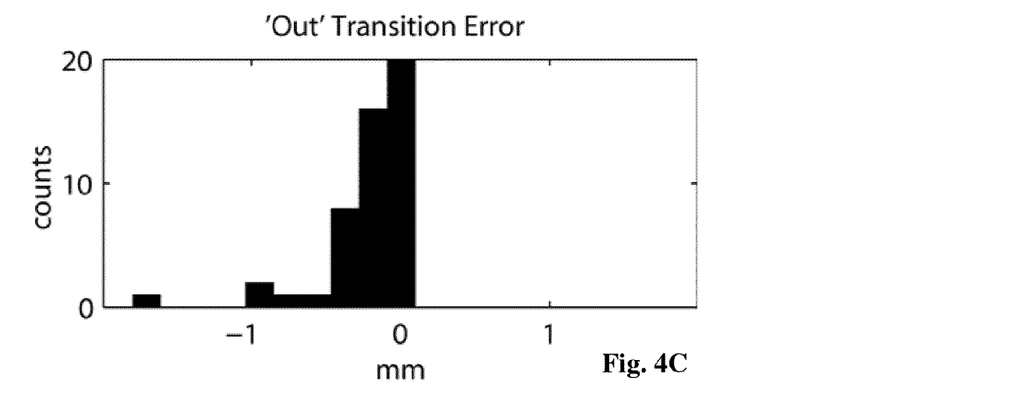

The HMM state sequence of the trajectory being tested was then inferred using the Viterbi algorithm, based on the trajectory's (clustered) NRMS and PSD sequence. FIGS. 3A-3D shows a typical trajectory's PSD (FIG. 3A) and NRMS (FIG. 3B) as well as the mean and maximum beta oscillatory activity used for clustering (FIG. 3C) relating to Patient 13, right STN in Table 1. FIG. 3D presents the tags resulting from clustering (blue line) together with the HMM inferred state sequence (green line). The inferred state transitions are noted by the steps in the state sequence (e.g. a step from state 1 to state 2 signifies the In transition etc.). In this example, the HMM transition inference concurs with the known (expert decision) In and Out transitions (solid red lines), but slightly precedes the known DLOR-ventral transition (dot-dash red line). For each transition (In, Out, and DLOR-ventral) the state transition error was defined as follows (Eq. 2):

$$\text{Error} = S - \hat{S} \quad (2)$$

where S is the known state transition defined by the neurophysiologist and $\hat{S}$ is the HMM inferred state transition (FIG. 3D, red lines and steps in the green line, respectively) in mm EDT. Hits and Correct Rejections (CRs) were the number of correctly detected and correctly negated transitions respectively. Hits did not take into account detection accuracy, it was simply used to count the number of inferred HMM transitions where there was also a known transition. All Hits, however, were within 2 mm, and 88% of Hits were within 0.5 mm of the known transitions (FIGS. 4A-4C). Misses were the number of transitions (according to the expert decision) that the HMM did not detect and False Alarms (FAs) were the number of HMM transition detections when by expert decision there was no transition. A histogram of the spatial errors in inferring the location of the state transitions can be seen in FIGS. 4A-4C and a summary of the results (including Hits, CRs, FAs, and Misses) can be seen in Table 4. Detection reliability (Table 4) was calculated by the sum of correct detections (Hits+CRs) divided by the total number of trajectories. A stricter calculation of detection reliability (limiting Hits to those with error<1 mm) is also presented in Table 4.

The In transition error described here (mean±SD: −0.09±0.35 mm) was better than that found by the Bayesian method both in mean and SD (Bayesian method, error=0.18±0.84 mm). The Out transition error (mean±SD: −0.20±0.33 mm) also demonstrated better mean and standard deviation (Bayesian method, error=0.50±0.59 mm). The DLOR-ventral transition detection is novel and therefore doesn't have a reference for comparison, but showed similar results to the In/Out detections (mean±SD: −0.27±0.58 mm).

The HMM algorithm had to deal with a heterogeneous variation of trajectories.

TABLE 4

A summary of the HMM transition detections, detection reliability and transition error results.

| | Correct detections | | Incorrect detections | | Reliability (correct detections) Total | | Mean Error | SD of Error |
|---|---|---|---|---|---|---|---|---|
| Transition | Hits | CR | Misses | FA | All Hits | Error < 1 mm | (mm) | (mm) |
| In | 56 | 0 | 0 | 0 | 100% | 95% | −0.09 | 0.35 |
| DLOR-ventral | 48 | 7 | 0 | 1 | 98% | 86% | −0.27 | 0.58 |
| Out | 49 | 3 | 4 | 0 | 93% | 91% | −0.20 | 0.33 |

The results presented are for all Hits (all Hits were within 2 mm of their known transitions, i.e. error<2 mm). Reliability is presented for all Hits as well as when limiting Hits to error<1 mm. CR, correct rejections; FA, false alarms; SD, standard deviation.

3. Discussion

The beneficial effects of bilateral STN DBS on motor symptoms and quality of life have been demonstrated in patients with advanced PD; however, adverse effects of cognitive deterioration or psychiatric complications have also been reported. Since the STN has separate sensorimotor, limbic, and cognitive/associative subterritories, it would seem probable that accurate implantation of the DBS macroelectrode within the sensorimotor region is essential for achieving therapeutic motor benefit while avoiding limbic or cognitive side effects. Hence, demarcation of the outer boundaries of the STN is not enough, and demarcation of the subterritories of the STN is required. Automatic methods presented to date use MER to localize only the outer boundaries of the STN. By adding beta PSD analysis and using an HMM, demarcation of subterritories within the STN is possible.

In this study, a very simple (and coarse) clustering technique provided good state inference of the MER trajectory by means of an HMM. Better accuracy than the Bayesian method for detecting STN entry/exit was achieved, with the addition of an intra-STN DLORventral transition detection. The HMM can be used offline to automatically detect the trajectory state transitions, or semi-online at the end of a trajectory during STN DBS surgery to help refine demarcation of the sensorimotor STN for macroelectrode implantation. Localization of the DLOR-ventral transition can aid the neurosurgeon in deciding which MER track to implant, when multiple electrodes are used for MER, and in implanting the macroelectrode at the optimal depth.

Positive therapeutic benefit to STN-DBS has been associated with proximity of the active macroelectrode contacts to the dorsolateral border of the STN. It has been proposed that this may be due to activation of adjacent structures such as the zona incerta and/or fields of Forel. It is possible that the benefits of STN dorsolateral border placement of the macroelectrode may also be due to avoidance of volume conduction to ventral areas, which have been associated with neuropsychological side effects. If this is the case then electrode distance from the DLOR-ventral border may be of primary importance in achieving optimal sensorimotor benefit without cognitive or limbic side effects.

The good results and robustness of the HMM in this study despite coarse clustering, indicate that higher resolution (calculated across a larger data set) in conjunction with a more advanced HMM—utilizing spike shape and discharge pattern—would probably provide even better results.

4. General Mapping Method

In another aspect, the present invention relates to a method for real-time mapping during surgery of a target region in the brain among a plurality of regions traversed by one or more electrodes, the method comprising the steps of:
(i) inserting the one or more electrodes into the brain according to a predetermined insertion trajectory;
(ii) advancing the one or more electrodes towards the estimated location of the target region;
(iii) recording neurophysiological activity by the one or more electrodes along the insertion trajectory;
(iv) calculating power spectral analysis values for the neurophysiological activity recorded along the insertion trajectory; and
(v) using a Dynamic Bayesian Network based on part or all of the calculated power spectral analysis values along the insertion trajectory to assign to each selected point along the insertion trajectory the region among the plurality of regions with the highest probability value thus identifying all the points wherein the one or more electrodes were in the target region.

The first step involves inserting one or more electrodes into the brain according to a predetermined insertion trajectory. Before surgery, a neurosurgeon uses magnetic resonance imaging (MRI), computed tomography (CT) scanning or any other available technology to identify and locate the exact target within the brain where the macroelectrode (chronic macroelectrode) should be inserted. An insertion trajectory is then calculated based on the identified target.

The number of electrodes to be inserted remains to the discretion of the medical team in charge of the procedure. Adding more electrodes increases the chances a trajectory to go through the optimal target location, while at the same time also increases the chances causing damage along the trajectory, for example, going through a small blood vessel. Typically, the medical team chooses one to five electrodes to be inserted.

The second step involves advancing the one or more electrodes towards the estimated location of the target region. Advancing continuously or in discreet steps, the number of steps to be taken and the size of each step are determined by the operating neurosurgeon. In certain embodiments, the size of each step becomes smaller as the electrode approaches the estimated target region.

The third step involves recording neurophysiological activity by the one or more electrodes along the insertion trajectory. The type of neurophysiological activity recorded may be different according to the target region to be reached. As detailed above, the STN shows increased and oscillatory activity for patients with Parkinson's disease (PD). In dystonia, the GPi (globus pallidus internal segment) may be bursty with a lower frequency than that seen in the STN of PD patients.

The fourth step involves calculating power spectral analysis values for the neurophysiological activity recorded along the insertion trajectory. In certain embodiments, normalized root mean square (NRMS) and power spectral analysis density (PSD) values for the neurophysiological activity are recorded along the insertion trajectory. PSD is a form of power spectral analysis.

The fifth step involves using a Dynamic Bayesian Network such as a Hidden Markov Model (HMM) based on part or all of the calculated power spectral analysis values along the insertion trajectory to assign to each selected point along the insertion trajectory, the region among the plurality of regions with the highest probability value thus identifying all the points wherein the one or more electrodes were in the target region.

The Dynamic Bayesian Network is fed with power spectral analysis values (in certain embodiments, NRMS and PSD values) for all the neurophysiological activity recorded along the insertion trajectory. The Dynamic Bayesian Network's role is to look at the data along the insertion trajectory, and predict statistically the region (or state) to be associated point along the insertion trajectory.

At a minimum, the Dynamic Bayesian Network or HMM should distinguish between two regions (states) inside the target region or outside the target region. In many cases, it is preferred to train the Dynamic Bayesian Network to distinguish between more than two regions (states).

Training the Dynamic Bayesian Network or HMM involves entering a statistically significant number of trajectory data reference cases comprising for each point along the insertion trajectory power spectral analysis values, where a human expert assigns to each point in the insertion trajectory, the correct region it is in. In certain embodiments, the Dynamic Bayesian Network comprises NRMS and PSD values. The Dynamic Bayesian Network then studies the statistical relations in the data of the reference cases, so that given a new case with only power spectral analysis values for points along the insertion trajectory, the Dynamic Bayesian Network can build a trajectory model assigning to each point along the insertion trajectory the state with the highest probability. Assigning the state takes into account not only the power spectral analysis values recorded at the step, but also the power spectral analysis values of part or all the points along the insertion trajectory. The Dynamic Bayesian Network trajectory model is captured in Tables 2 and 3, which serve as a statistical reference based for analyzing new insertion trajectories and assigning the highest probability state to each location along the insertion trajectory.

In certain embodiments, the method further comprises the step of removing the one or more electrodes and inserting a macroelectrode in the identified DLOR of the STN for producing deep brain simulation for treatment of Parkinson's disease.

In certain embodiments, the one or more electrodes are microelectrodes, macroelectrodes or both. Microelectrodes offer a higher resolution of the data by being able to advance in smaller-size steps, but it is also possible to use macroelectrodes. It is also possible to combine insertion of both microelectrodes and macroelectrodes.

In certain embodiments, the one or more electrodes are advanced towards the estimated location of the DLOR of the STN continuously; in small discrete steps of equal size; in small discrete steps of variable size; or any combination thereof. For example, it is possible to advance continuously with the electrode(s) until arriving to a destination point. Alternatively, it is possible to advance continuously with the electrode(s), until a certain point and then advance in discreet steps of a fixed or variable size.

In certain embodiments, the power spectral analysis values are obtained by using power spectral density (PSD) calculations though it is possible to use other power spectral analysis methods according to the invention.

In certain embodiments, the method further comprises the step of calculating normalized Root mean square (NRMS) values for the recorded neurophysiological activity.

In certain embodiments, the Dynamic Bayesian Network is a Hidden Markov Model (HMM) though it is possible to use other Dynamic Bayesian Network algorithms with the invention.

In certain embodiments, the method further comprises an initial step of training the Dynamic Bayesian Network by providing reference data of a statistically-significant number of insertion trajectories wherein points along each insertion trajectory are assigned by an expert to one of the following regions: 1. the DLOR of the STN; 2. the region in the insertion trajectory before the STN; 3. the region inside the nonoscillatory STN; or 4. the region in the insertion trajectory after the STN.

The present invention also relates to a system for real-time mapping during surgery of a target region in the brain among a plurality of regions traversed by one or more electrodes, the system comprising:

(i) one or more electrodes inserted into the brain according to a predetermined insertion trajectory;

(ii) advancing means for advancing the one or more electrodes towards the estimated location of said target region;

(iii) a recording unit for recording neurophysiological activity by the one or more electrodes along the insertion trajectory;

(iv) first data processing means for calculating power spectral analysis values for the neurophysiological activity recorded the insertion trajectory; and (v) second data processing means for using a Dynamic Bayesian Network based on part or all of the calculated power spectral analysis values along the insertion trajectory to assign to each selected point along the insertion trajectory a region among said plurality of regions with the highest probability value.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a sub-combination or variation of a sub-combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the invention.

REFERENCES

1. Machado A, Rezai A R, Kopell B H, Gross R E, Sharan A D, Benabid A L. Deep brain stimulation for Parkinson's disease: surgical technique and perioperative management. Mov Disord 2006; 21: S247-S258.
2. Herzog J, Fietzek U, Hamel W, et al. Most effective stimulation site in subthalamic deep brain stimulation for Parkinson's disease. Mov Disord 2004; 19:1050-1054.
3. Chen C C, Pogosyan A, Zrinzo L U, et al. Intra-operative recordings of local field potentials can help localize the subthalamic nucleus in Parkinson's disease surgery. Exp Neurol 2006; 198: 214-221.
4. Falkenberg J H, McNames J, Favre J, Burchiel K J. Automatic analysis and visualization of microelectrode recording trajectories to the subthalamic nucleus: preliminary results. Stereotact Funct Neurosurg 2006; 84:35-44.
5. Moran A, Bar-Gad I, Bergman H, Israel Z. Real-time refinement of subthalamic nucleus targeting using Bayesian decision-making on the root mean square measure. Mov Disord 2006; 21:1425-1431.
30. Novak P, Daniluk S, Ellias S A, Nazzaro J M. Detection of the subthalamic nucleus in microelectrographic recordings in Parkinson disease using the high-frequency (>500 Hz) neuronal background: technical note. J Neurosurg 2007; 106:175-179.
6. Danish S F, Baltuch G H, Jaggi J L, Wong S. Determination of subthalamic nucleus location by quantitative analysis of despiked background neural activity from microelectrode recordings obtained during deep brain stimulation surgery. J Clin Neurophysiol 2008; 25:98-103.
7. Zaidel A, Spivak A, Shpigelman L, Bergman H, Israel Z (2009) Delimiting subterritories of the human subthalamic nucleus by means of microelectrode recordings and a Hidden Markov Model. Mov Disord 24:1785-1793.

The invention claimed is:

1. A method for real-time mapping during surgery of subterritories of the subthalamic nucleus (STN) in the brain, the method comprising the steps of:
(i) inserting one or more electrodes into the brain according to a predetermined insertion trajectory;
(ii) advancing said one or more electrodes towards the estimated location of a dorsolateral oscillatory region (DLOR) of the STN;
(iii) recording beta oscillatory activity by said one or more electrodes along the insertion trajectory;
(iv) calculating power spectral analysis values for the beta oscillatory activity recorded along the insertion trajectory; and
(v) using a Hidden Markov Model (HMM) based on part or all of the calculated power spectral analysis values along the insertion trajectory for detecting the borders of said DLOR and assigning to each selected point along the insertion trajectory one of the following regions with the highest probability value: 1. the DLOR of the STN; 2. the region in the insertion trajectory before the STN; 3. the region inside the non-oscillatory STN; or 4. the region in the insertion trajectory after the STN, thereby detecting borders of said subterritories of the STN in the brain.

2. A method according to claim 1, further comprising the step of removing said one or more electrodes and inserting a macroelectrode in the identified DLOR of the STN for producing deep brain simulation for treatment of Parkinson's disease.

3. A method according to claim 1, wherein said one or more electrodes are microelectrodes, macroelectrodes or both.

4. A method according to claim 1, wherein said one or more electrodes are advanced towards the estimated location of said DLOR of the STN continuously; in small discrete steps of equal size; in small discrete steps of variable size; or any combination thereof.

5. A method according to claim 1, wherein the power spectral analysis values are obtained by using power spectral density (PSD) calculations.

6. A method according to claim 1, further comprising the step of calculating normalized Root mean square (NRMS) values for the recorded beta oscillatory activity.

7. A method according to claim 6, wherein root mean square (RMS) values for the beta oscillatory activity recorded along the insertion trajectory are calculated by applying the formula $$RMS(\overline{X}) = \sqrt{\frac{\sum_{i=1}^{n}(X_i - \mu)^2}{n-1}}$$

where X is the vector of a sampled analog signal with mean μ, Xi is each sample, and n is the number of samples, and the RMS values are then normalized to obtain NRMS values.

8. A method according to claim 1, further comprising an initial step of training the HMM by providing reference data of a statistically-significant number of insertion trajectories wherein points along each insertion trajectory are assigned by an expert to one of the following regions: 1. the DLOR of the STN; 2. the region in the insertion trajectory before the STN; 3. the region inside the nonoscillatory STN; or 4. the region in the insertion trajectory after the STN.

9. A system for real-time mapping during surgery of subterritories of the subthalamic nucleus (STN) in the brain, the system comprising:
(i) one or more electrodes configured to be inserted into the brain according to a predetermined insertion trajectory;
(ii) advancing means for advancing said one or more electrodes towards the estimated location of a dorsolateral oscillatory region (DLOR) of the STN;
(iii) a recording unit for recording beta oscillatory activity by said one or more electrodes along the insertion trajectory;
(iv) first data processing means for calculating power spectral analysis values for the beta oscillatory activity recorded along the insertion trajectory; and
(v) second data processing means for using a Hidden Markov Model (HMM) based on part or all of the calculated power spectral analysis values along the insertion trajectory for detecting the borders of said DLOR and assigning to each selected point along the insertion trajectory one of the following regions with the highest probability value: 1. the DLOR of the STN; 2. the region in the insertion trajectory before the STN; 3. the region inside the nonoscillatory STN; or 4. the region in the insertion trajectory after the STN, thereby detecting borders of said subterritories of the STN in the brain.

* * * * *